(12) United States Patent
Smoliarov et al.

(10) Patent No.: US 6,626,871 B1
(45) Date of Patent: Sep. 30, 2003

(54) METHOD AND APPARATUS FOR REMOVING CAP FROM MEDICAL DEVICE

(75) Inventors: Boris V. Smoliarov, Voronezh (RU); Victor T. Rogatchev, Voronezh (RU); Victor N. Katov, Voronezh (RU); Alan Felton, Lenexa, KS (US); Nathaniel Leon, Lutherville, MD (US)

(73) Assignee: Felton International, Inc., Lenexa, KS (US)

( * ) Notice: Subject to any disclaimer, the term of this patent is extended or adjusted under 35 U.S.C. 154(b) by 10 days.

(21) Appl. No.: 09/685,633

(22) Filed: Oct. 10, 2000

(30) Foreign Application Priority Data

Oct. 11, 1999 (RU) .............................. 99121141
Nov. 23, 1999 (RU) .......................... 99124268

(51) Int. Cl.⁷ .............................................. A61M 5/00
(52) U.S. Cl. ..................... 604/263; 604/70; 128/919
(58) Field of Search ..................... 604/15–16, 188–189, 604/192, 152, 150, 263, 199, 218, 256, 58, 164.08, 156, 68, 70, 71; 128/919

(56) References Cited

U.S. PATENT DOCUMENTS

| | | |
|---|---|---|
| 2,821,891 A | 2/1958 | Gorey |
| 3,057,349 A | 10/1962 | Ismach |
| 3,292,622 A | 12/1966 | Banker |
| 3,461,867 A | 8/1969 | Zimmet et al. |
| 3,515,130 A | 6/1970 | Tsujino |
| 3,518,990 A | 7/1970 | Banker |
| 3,540,444 A | 11/1970 | Moreland |
| 3,788,315 A | 1/1974 | Laurens |
| 3,853,125 A | 12/1974 | Clark et al. |

(List continued on next page.)

FOREIGN PATENT DOCUMENTS

| | | |
|---|---|---|
| EP | 0526772 | 10/1993 |
| EP | 0776224 B1 | 8/1995 |
| EP | 0888790 A1 | 7/1997 |
| EP | 0834330 | 4/1998 |
| EP | 0788386 B1 | 1/1999 |
| EP | 0888791 A1 | 1/1999 |
| EP | 0799064 B1 | 8/1999 |
| EP | 0951917 A3 | 10/1999 |
| EP | 0951917 A2 | 10/1999 |
| FR | 2629348 | 3/1988 |
| FR | 2629348 | 10/1989 |
| FR | 2641190 | 7/1990 |
| RO | 0106078 | 2/1993 |
| RO | 0108150 | 2/1994 |
| WO | 9734652 A1 | 9/1997 |
| WO | 9748485 A1 | 12/1997 |
| WO | 9810750 A1 | 3/1998 |
| WO | 9813087 | 4/1998 |
| WO | 9813470 A1 | 4/1998 |
| WO | 9821364 A2 | 5/1998 |
| WO | 9901168 A1 | 1/1999 |
| WO | 9901169 A1 | 1/1999 |
| WO | 9908689 A1 | 2/1999 |
| WO | 9927961 A1 | 6/1999 |
| WO | 0013573 A1 | 3/2000 |
| WO | 0014547 A1 | 3/2000 |
| WO | 0019982 A1 | 4/2000 |
| WO | 0023592 A3 | 4/2000 |
| WO | 0023592 A2 | 4/2000 |
| WO | 0026385 A1 | 5/2000 |

*Primary Examiner*—Manuel Mendez
*Assistant Examiner*—Mark K. Han
(74) *Attorney, Agent, or Firm*—Mayer Brown Rowe & Maw LLP; Joseph A. Mahoney; Christine M. Rebman

(57) ABSTRACT

Disclosed is medical device, such as a mass injector, that has a protective cap disposed on it that minimizes or eliminates cross contamination, wherein the cap can be ejected in a quick manner.

20 Claims, 3 Drawing Sheets

U.S. PATENT DOCUMENTS

| | | |
|---|---|---|
| 4,103,684 A | 8/1978 | Ismach |
| 4,124,024 A | 11/1978 | Schwebel et al. |
| 4,165,739 A | 8/1979 | Doherty et al. |
| 4,266,541 A | 5/1981 | Landau |
| 4,403,986 A | 9/1983 | Dettbarn et al. |
| 4,592,742 A | 6/1986 | Landau |
| 4,596,556 A | 6/1986 | Morrow et al. |
| 4,722,728 A | 2/1988 | Dixon |
| 4,850,967 A | 7/1989 | Cosmai |
| 4,874,367 A | 10/1989 | Edwards |
| 4,913,699 A | 4/1990 | Parsons |
| 5,000,737 A | 3/1991 | Free et al. |
| 5,024,656 A | 6/1991 | Gasaway et al. |
| 5,049,125 A | 9/1991 | Accaries et al. |
| 5,062,830 A | 11/1991 | Dunlap |
| 5,063,905 A | 11/1991 | Farrell |
| 5,085,647 A | 2/1992 | Henderson et al. |
| 5,152,751 A | 10/1992 | Kozlowski |
| 5,171,304 A | 12/1992 | Ris et al. |
| 5,190,523 A | 3/1993 | Lindmayer |
| 5,222,948 A | 6/1993 | Austin et al. |
| 5,256,142 A | 10/1993 | Colavecchio |
| 5,279,608 A | 1/1994 | Cherif Cheikh |
| 5,334,144 A | 8/1994 | Alchas et al. |
| 5,354,286 A | 10/1994 | Mesa et al. |
| 5,399,163 A | 3/1995 | Peterson et al. |
| 5,411,492 A | 5/1995 | Sturman et al. |
| 5,456,388 A | 10/1995 | Honstein et al. |
| 5,501,666 A | 3/1996 | Spielberg |
| 5,503,627 A | 4/1996 | McKinnon et al. |
| 5,512,043 A | 4/1996 | Verkaart |
| 5,520,639 A | 5/1996 | Peterson et al. |
| 5,536,249 A | 7/1996 | Castellano et al. |
| 5,569,189 A | 10/1996 | Parsons |
| 5,569,209 A | 10/1996 | Roitman |
| 5,573,767 A | 11/1996 | Dufour et al. |
| 5,584,182 A | 12/1996 | Althaus et al. |
| 5,593,390 A | 1/1997 | Castellano et al. |
| 5,599,302 A | 2/1997 | Lilley et al. |
| 5,618,268 A | 4/1997 | Raines et al. |
| 5,620,434 A | 4/1997 | Brony |
| 5,643,211 A | 7/1997 | Sadowski et al. |
| 5,697,917 A | 12/1997 | Sadowski et al. |
| 5,704,911 A | 1/1998 | Parsons |
| 5,713,875 A | 2/1998 | Tanner, II |
| 5,716,346 A | 2/1998 | Farris |
| 5,722,953 A | 3/1998 | Schiff et al. |
| 5,728,074 A | 3/1998 | Castellano et al. |
| 5,730,723 A | 3/1998 | Castellano et al. |
| 5,733,600 A | 3/1998 | McCabe |
| 5,746,714 A | 5/1998 | Salo et al. |
| 5,746,733 A | 5/1998 | Capaccio et al. |
| 5,755,696 A | 5/1998 | Caizza |
| 5,769,138 A | 6/1998 | Sadowski et al. |
| 5,776,125 A | 7/1998 | Dudar et al. |
| 5,780,100 A | 7/1998 | McCabe et al. |
| 5,782,802 A | 7/1998 | Landau |
| 5,785,688 A | 7/1998 | Joshi et al. |
| 5,788,675 A | 8/1998 | Mayer |
| 5,800,388 A | 9/1998 | Schiff et al. |
| 5,803,078 A | 9/1998 | Brauner |
| 5,807,374 A | 9/1998 | Caizza et al. |
| 5,814,024 A | 9/1998 | Thomson et al. |
| 5,817,082 A | 10/1998 | Niedospial, Jr. et al. |
| 5,820,601 A | 10/1998 | Mayer |
| 5,820,621 A | 10/1998 | Yale et al. |
| 5,827,244 A | 10/1998 | Boettger |
| 5,830,193 A | 11/1998 | Higashikawa |
| 5,832,971 A | 11/1998 | Yale et al. |
| 5,833,213 A | 11/1998 | Ryan |
| 5,833,668 A | 11/1998 | Aguilar |
| 5,833,674 A | 11/1998 | Turnbull et al. |
| 5,836,911 A | 11/1998 | Marzynski et al. |
| 5,836,923 A | 11/1998 | Mayer |
| 5,839,715 A | 11/1998 | Leinsing |
| 5,840,061 A | 11/1998 | Menne et al. |
| 5,840,062 A | 11/1998 | Gumaste et al. |
| 5,846,233 A | 12/1998 | Lilley et al. |
| 5,851,198 A | 12/1998 | Castellano et al. |
| 5,858,001 A | 1/1999 | Tsals et al. |
| 5,860,957 A | 1/1999 | Jacobsen et al. |
| 5,860,961 A | 1/1999 | Gettig |
| 5,860,962 A | 1/1999 | Lewandowski et al. |
| 5,865,796 A | 2/1999 | McCabe |
| 5,899,880 A | 5/1999 | Bellhouse et al. |
| 5,922,685 A | 7/1999 | Rakhmilevich et al. |
| 5,938,637 A | 8/1999 | Austin et al. |
| 6,004,286 A | 12/1999 | Bellhouse et al. |
| 6,010,478 A | 1/2000 | Bellhouse et al. |
| 6,013,050 A | 1/2000 | Bellhouse et al. |
| D422,697 S | 4/2000 | Bellhouse et al. |
| 6,053,889 A | 4/2000 | Heinzen et al. |
| D428,650 S | 7/2000 | Bellhouse et al. |
| 6,083,197 A | 7/2000 | Umbaugh |
| 6,102,896 A | 8/2000 | Roser |
| 6,183,449 B1 * | 2/2001 | Sibbitt .................. 604/263 |

* cited by examiner

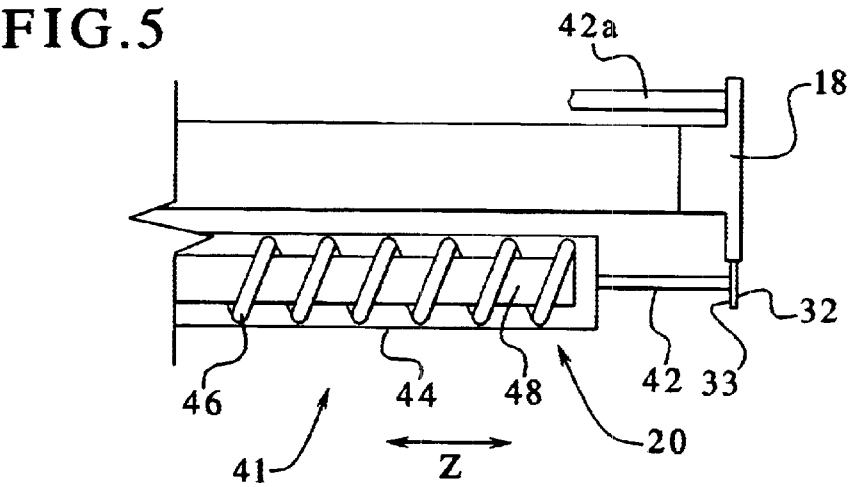
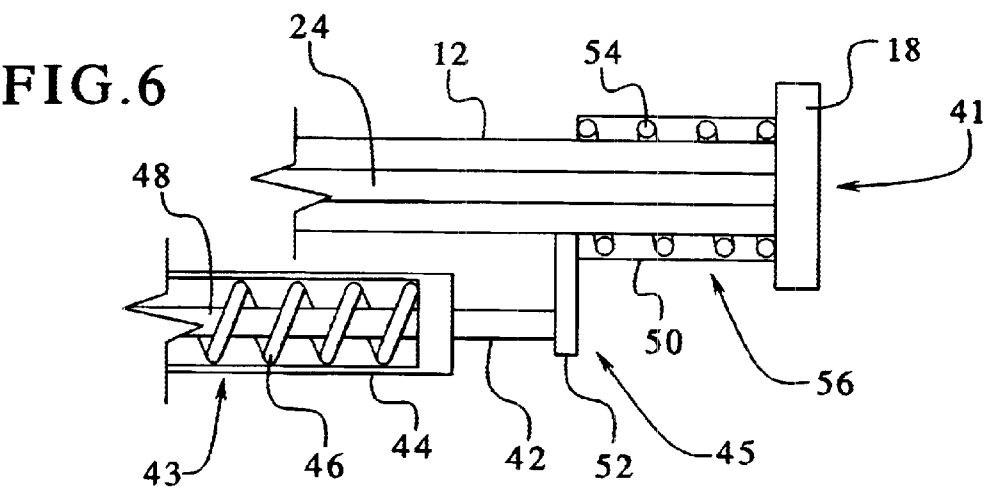
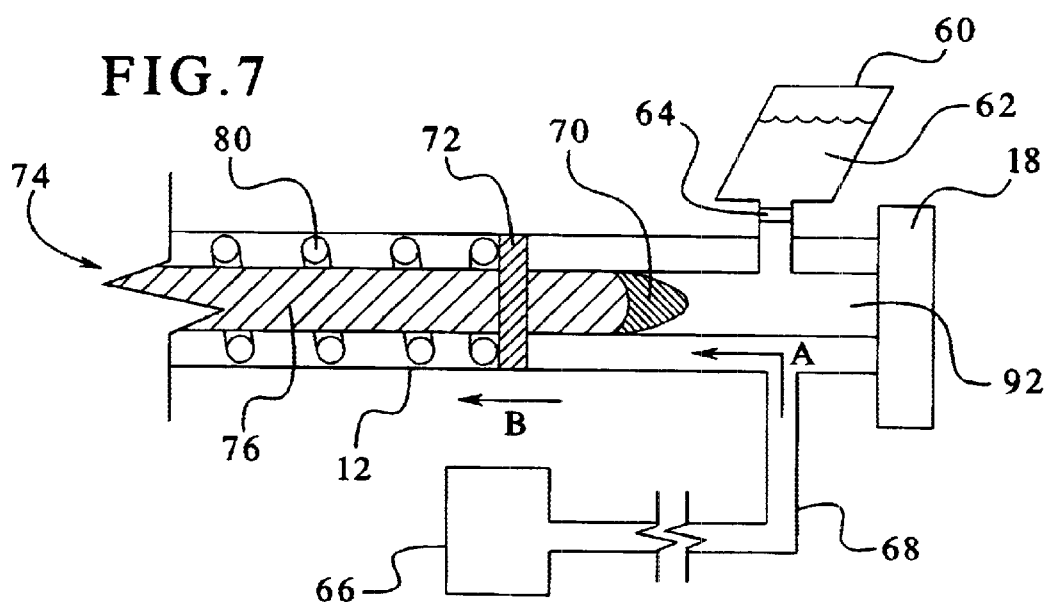

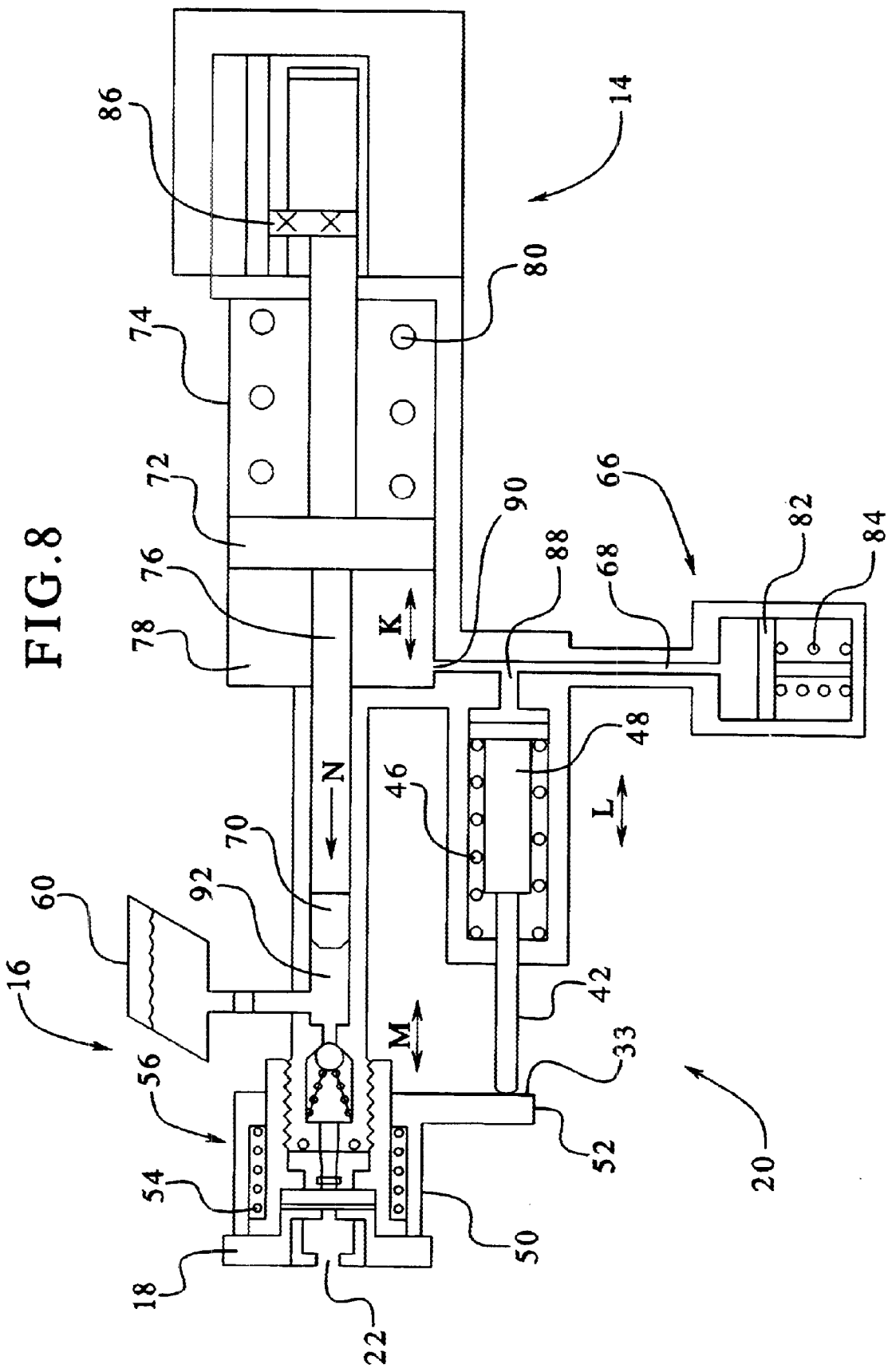

METHOD AND APPARATUS FOR REMOVING CAP FROM MEDICAL DEVICE

CROSS REFERENCE OF RELATED APPLICATIONS

This application claims priority to, and benefit from, Russian Patent Application 99124268, filed Nov. 23, 1999, now issued as Russian Patent No. 2152228; and Russian Patent Application 99121141, filed Oct. 12, 1999; now issued as Russian Patent No. 2152227 the disclosures of which are entirely incorporated by reference herein.

TECHNICAL FIELD OF THE INVENTION

The invention relates to a medical device having a mechanism that protects against cross contamination by utilizing a removable cap.

BACKGROUND OF THE INVENTION

The most effective measure to prevent many diseases is the mass immunization with vaccines. Since medical science has come to understand the principles of viral theory and its importance to the transmission of diseases, the need to break the viral or bacterial transmission chain from host to host has become well-established. There are wide varieties of methodologies accepted by medical science to break the chain depending on the requirements of the situation. The most stringent protocols include: sterilization, disinfection, and sanitation utilizing heat chemicals and/or ionizing radiation.

Barriers are another common protocol and can be as simple as establishing an imaginary boundary where one side of the boundary is kept clean and the other is defined as contaminated. Any object being transferred from the clean to the contaminated side of the boundary is not returned to the clean side without being disinfected, sanitized, or sterilized. A typical example of this type of protocol is within the medical surgical fields. The surface of the operating table is defined as the boundary. Any item that is dropped below the surface of the operating table is immediately defined as contaminated. This includes surgical implements or the surgeon's hands.

With needle injection devices there are two common protocols both of which start from the premise that a used syringe is, by definition, contaminated. The first, which is commonly used in dentistry, uses syringes and sometimes needles that are sterilized after each use. The second is more commonly used in general medicine in the U.S. and other developed countries. This is the disposable syringe and needle assembly. Because of the low cost of production typically—less than $0.10 per syringe assembly—this protocol is well-accepted.

Jet injector systems on the other hand continue to be characterized by relatively high cost per injection ($1.00 or more) when the syringe portion of the injector is discarded with each use. Additionally, there is the challenge in developing countries where lack of understanding of viral theory and/or a general hoarding mentality discourages following generally accepted protocols within all aspects of health and hygiene. With the identification of blood-borne pathogens like HIV, Hepatitis B, Hepatitis C and others, the need to follow proper protocols becomes more critical.

In the past, jet injectors such as Ped-O-Jet®, Ammo-Jet®, and similar mass campaign jet injectors were brought to health care systems. Such injectors had no provision for preventing the transfer of blood-borne pathogens except through the complicated disassembly and disinfecting process. In mass immunization campaigns these types of injector systems fell out of favor starting in the mid and late 1980's when it was determined that bodily fluids are easily transmitted from one patient to another.

To eliminate the possible transmission of blood-borne pathogens between individuals, disposable or partially disposable jet injector systems were developed. Bio-Jet®, J-'Tip®, and others characterize this type of jet injector. General acceptance of these units is limited by relatively high direct costs, even in developed countries like the United States. The standard paradigm of breaking the contamination transmission chain has been addressed by either syringe disposal or designing the syringe so it can easily be decontaminated. Currently, there exists a steadily growing danger of the epidemic diseases (AIDS, hepatitis, tuberculosis and other viral diseases transferred through blood) being transmitted between individuals through the use of needleless injectors.

The traditional needleless injectors comprise the basic design, a housing with an inner power unit, a medication unit, and a nozzle. The function of the power unit pumps the medication into an under-plunger cavity of the medication unit chamber and to expel the medication through the nozzle.

At the initial stage of needleless injector development, when no check valves were used as a control for the functioning of the medication chamber, a method to prevent foreign particles from entering the injector nozzle was to use a sealed nozzle cap. Such cap was limited by the filling of the medication chamber with medication and could not guarantee contamination prevention.

Another approach to the contamination prevention problem has been the use of a disposable, low cost, one-shot nozzle assembly for jet injectors. The nozzle assembly comprises a two-piece molded device incorporating a generally cylindrical nozzle body having a central longitudinal bore of a predefined diameter, extending from a proximal end of the nozzle towards its distal end, terminating in a conical portion of the nozzle. A very small diameter jet-forming bore is formed at the apex of the conical portion of the bore in general. The disadvantage of this device is its lower efficiency (i.e., low vaccination rate) because of poor flow due to the conical design. Moreover, a plastic nozzle element also increases the vaccination cost.

A typical jet injector design has additional drawbacks. Even in the practice of using a protective cap, there is a possibility of infection transfer from one person to another by means of fluids (blood, lymph, medication) reflected from the skin surface during injection ("back splash") that may get on the nozzle and be transferred from one patient to the next. The protective cap can be a one-shot cap, including the injection nozzle. A purpose of this device is to prevent the multiple use of a cap with a nozzle. This is achieved through the removal, replacement, and/or destruction of the cap at the later stage of the injection. However, cross-contamination continues to be problematic because in the injection stage, the contaminated matter can be transferred through the nozzle to inside the injector such as, for example, into the cavity and be transmitted to a new patient through a new cap and nozzle.

With all the known devices, there is no guarantee that the minimum safety requirements for cross-contamination prevention, as recently introduced (Glenn Austin et al., *Gross Contamination Testing of Vaccine Jet Injectors, A Preliminary Report*, PATH, Seattle, Wash., 98109), will be achieved. Other studies indicate a very dangerous situation. For example, Russian and Brazilian studies have shown unfavorable data in up to 1.0% of the subjects studied—a level of risk far too great to ignore.

When jet injectors were introduced in the 1940's, they were popular for needle phobic patients or small veined patients. Improvements permitted jet injectors to administer hundreds of millions of vaccinations that saved countless lives. However, when the discovery of pathogen transfer occurred, jet injectors fell out of favour to such an extent that the WHO and the US Department of Defense no longer recommended jet injector use.

For example, in the mid- 1980's an outbreak of Hepatitis B was caused by use of one high workload injector in a weight loss clinic. See, Canter et al., An Outbreak of Hepatitis B Associated With Jet Injections In A Weight Loss Clinic, Arch. Intern. Med., 150:1923–1927 (1990).

Present parenteral injection technology has recently been deemed by the World Health Organization (WHO) to be incompatible with their requirements for the planned Global Programme of Vaccination and Immunization (GPV) initiatives. It is estimated that 6 additional parenteral vaccines will be recommended for childhood vaccination by the year 2005, requiring a total of 3.6 billion immunization injections per year. The total number of parenteral injections, including injected drugs as well as vaccines, will be roughly ten times this number. This is in addition to the hundreds of millions needed in military induction centers, epidemic situations, worldwide immunizations, and veterinary uses. Major health care providers such as UNICEF, the WHO and CDC have recently confirmed that a radical new technology is required that can be used by personnel with minimal training and that is safer, more convenient, and more comfortable than the syringe and needle. (Jodar L., Aguado T., Lloyd J. and Lambert P-H,(1998) Revolutionizing Immunizations Gen. Eng. News 18, p. 6.)

In other words, what used to be a continent wide life saver, became an undesirable product. The present invention solves problems associated with pathogen transfer and solves many problems associated with the high costs of disposable units.

In addition, other problems with mass injection involve time and labor. For example, to replace the cap each time manually expends significant time, especially when considering the hundreds, if not thousands, of inoculations that are needed. To this end, a device that permits easier removal of the cap and replacement is substantially needed.

Accordingly, there is a need in the art of needleless injection devices to solve the problem of cross-contamination during mass vaccinations. More particularly, there is a need for a protector designed for the nozzle head of needleless injectors, which halts "back splash" contamination, and which is low enough in cost to ensure its practical application as a disposable unit even for mass vaccinations.

SUMMARY OF THE INVENTION

The foregoing problems are solved and a technical advance is achieved by the present invention. Disclosed is medical device, such as a mass injector, that has a protective cap disposed on it that minimizes or eliminates cross contamination, wherein the cap can be ejected in a quick manner.

BRIEF DESCRIPTION OF THE DRAWINGS

FIG. 5 demonstrates another embodiment of the present invention.

FIG. 6 demonstrates yet another embodiment of the present invention.

FIG. 7 demonstrates yet another embodiment of the present invention.

FIG. 8 is yet another embodiment of the present invention.

DETAILED DESCRIPTION OF THE INVENTION

Figure 1:
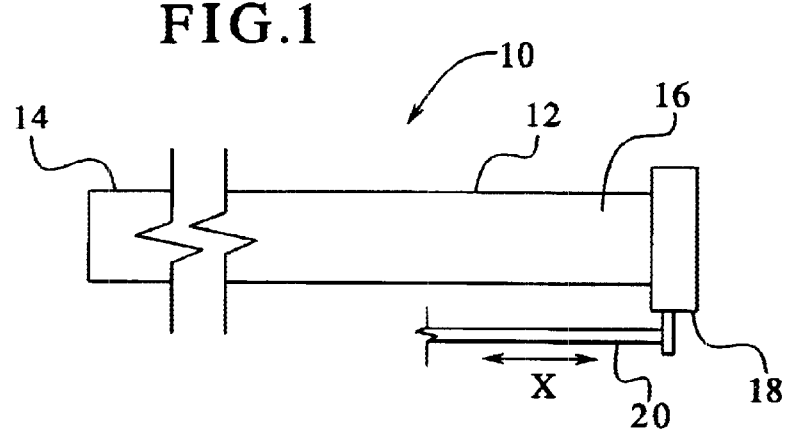
FIG. 1 demonstrates a simple embodiment of the invention.

FIG. 1 demonstrates a simple embodiment of the invention. The device 10 is shown having a main body 12, with the main body 12 further having a main body proximal end 14 and a main body distal end 16. A protective cap 18 is shown disposed near the main body distal end 16. The cap 18 can be detachably attached to the main body distal end 16 using conventional techniques, such as friction fits, bayonet fixing, male-female receptacles, or the like. Also shown is a means or mechanism for removing 20 the detachably attached cap 18. In this particular embodiment, the means for removing 20 the cap is a rod that pushes against a cap extension. Although not shown, the means for removing 20 can be attached to the main body 12. In this regard, as the means moves in the direction indicated by movement arrow X, the cap 18 is pushed off the distal end 16.

Figure 2:
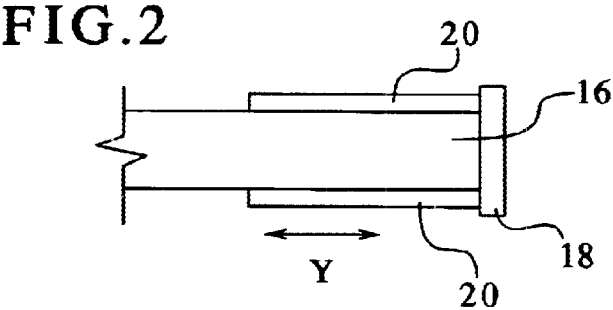
FIG. 2 demonstrates another embodiment of the present invention.

FIG. 2 demonstrates another embodiment of the present invention. Shown again is the protective cap 18 disposed at or near the main body distal end 16. In this embodiment however, the mechanism or means for removing 20 the cap is not a rod, but a collar or sleeve. In this regard, as the collar moves in the direction designated by arrow Y, the cap 18 is popped off. This permits a greater degree of contact between the cap 18 and the means 20 to permit the ejection of the cap 18.

Figure 3:
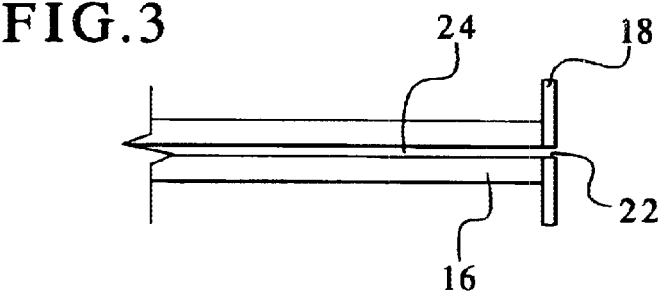
FIG. 3 demonstrates a cross section view of the cap and body.

FIG. 3 demonstrates a cross section view of the cap 18 and body 12. Shown in this embodiment is a cap orifice 22 that is coincident with a main body lumen 24. Injected medicines will pass through the lumen 24 and through the cap orifice 22.

Figure 4:
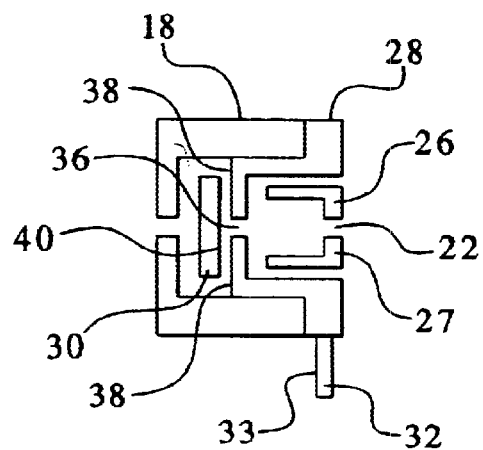
FIG. 4 describes another embodiment of the present invention, particularly the cap.

FIG. 4 describes another embodiment of the present invention, particularly the cap 18. To minimize cross contamination, the cap 18 can be configured in various ways. For example, an insert 26 having an insert orifice 27 can be used. Insert 26 can be inserted into a baffle 28. The baffle 28 can also include a protective film 30 disposed near or on the baffle 28. The cap 18 can also include a cap flange 32. The flange 32 can have a flange proximal face 33. Therefore, in a simple embodiment, the means for removing 20 the cap could contact the flange proximal face 33. Also include in the cap can be a baffle orifice 36 to further the goal of transmitting medication therethrough. The baffle may also include a baffle proximal face 38 upon which, as shown in FIG. 4, the film 30 may be disposed by coinciding a film distal face 40 to the baffle proximal face 38.

However, it should be noted that the film need not be solely found proximal to the baffle. The film 30 or a plurality of films can be located proximal to the baffle, distal to the baffle, proximal to the insert, distal to the insert, or sandwiched in between the insert and baffle. On the other hand, if many films are used, then the films may be disposed at any location deemed proper. In addition, the many components of the cap are optional. For example a cap need not have a cap flange 32 if a collar means 20 is used. Furthermore, an insert or baffle may not be necessary. Other configurations are described in copending U.S. Patent Application filed on Oct. 10, 2000, under attorney docket number 70006780-0004, entitled Universal Anti-Infectious Protector For Needleless Injectors, by the inventors B. Smolyarov, V. Rogachev, V. Katov, A. Felton, and N. Leon, the disclosure of which is entirely incorporated by reference herein.

FIG. 5 demonstrates another embodiment of the present invention. The means for removing 20 is shown in a cutaway view. The means for removing 20 may comprise an ejection assembly 41. In the simple embodiment of FIG. 1, the means for removing 20 can comprise an ejection assembly that comprises the rod shown. However, in FIG. 5, the ejection assembly can further comprise an ejector rod 42 (or an ejector rod 42a or collar 42a wherein no flange is needed), an ejector body 44, and may further include a mechanism or means 46 for biasing the ejector rod. In one embodiment, the means 46 for biasing may include a spring to bias the rod in the directions indicated by arrow Z.

However, it should be noted that the means for biasing can also include those means known in the art and can further include, but is not limited to, pistons, gears, rods, springs, worm gears, screws, electromagnets, optical components, and jacks. The means for biasing may also include various driving mechanisms, such as pneumatics, hydraulics, or manual drives. In addition, the means for biasing may also include phase change materials or other shape memory materials, such as those materials that change size or shape due to temperature application. One such material is Nitinol, which allows for size or shape transformation in its austenite and martensite states. Accordingly, the means for biasing is meant to include not only the structures described herein, but also, any acts or materials described herein, and also include any equivalent structures, equivalent acts, or equivalent materials; or equivalent structures, act equivalents, or material equivalents, to those described herein.

FIG. 6 demonstrates yet another embodiment of the present invention. Shown is an ejection assembly 41 comprising a first ejector 43 and a second ejector 45. The first ejector 43 may further include an ejector body 44, which may further comprise a means 46 for biasing an ejector rod 42. The second ejector 45 may include a collar, rod, or nozzle 56, or a means for biasing the nozzle. The nozzle 56 may comprise a nozzle sleeve 50 and a nozzle flange 52. Nozzle 56 may also include a means 54 for biasing the nozzle such as a spring. In this embodiment, the means for biasing the rod 42 may also bias the nozzle flange 52, thus causing the nozzle sleeve 50 to bias against the cap 18, thereby causing the cap to pop off. Once the means 46 for biasing the rod 42 is released, the means 54 for biasing the nozzle can then return the nozzle sleeve 50 back into position. Therefore, it is contemplated that the ejection assembly may include: (a) just the first ejector, (b) just the second ejector, (c) both ejectors, (d) both ejectors plus other components, or (e) any combination thereof. In this regard, the means 20 for removing the cap 18 may be the ejection assembly as defined herein.

FIG. 7 demonstrates yet another embodiment of the present invention. In this embodiment, more detail of the injection system is shown. A medication vial 60 containing medication 62 (in one embodiment an aqueous solution) is shown detachably attached to the injector system. A check valve 64 is disposed along the connection to moderate medication flow. Also shown is a hydraulic assembly 66 that is connected to the injector system via hose 68. The injector system comprises an injector head, which is attached to a plunger 72. These components may be found in a cylinder 74, which may comprise the main body 12. Within the cylinder may be a cylinder piston 76, which itself may be within a cylinder chamber 78. The cylinder piston 76 can be driven by another biasing means 80, such as a spring or the other means described herein. Functionally, as hydraulic pressure is applied in the direction marked by arrow A, the plunger 72 is driven in the direction of arrow B. The plunger movement causes the biasing means 80 to compress. In addition, the plunger movement causes medication 60 to enter into cylinder chamber 78 distal to injector head 70. Once the hydraulic pressure is removed, the means 80 biases the plunger and it moves in the direction opposite to arrow B, thereby driving the medication into the cap 18 and therethrough.

It should be noted that in any embodiment of the present invention, the medication need not be liquid. In addition to aqueous solutions, the present invention may employ suspensions, aqueous gels, emulsions, or controlled release injectable medications. One other dosage form includes powder. For example, Powdeiject Pharmaceuticals, of Oxford, United Kingdom, and/or Powdeiject Vaccines (Madison, Wis.) have developed an injector that propels medicine in powder form in the same manner as traditional needleless injectors. For example, see, U.S. Pat. Nos. 5,733,600; 6,053,889; and 5,899,880, the disclosures of which are expressly and entirely incorporated herein. Since the powder form of drugs take up less than 1% of the volume of drugs in liquid form, adapting the powder injectors to be used in accordance with the present invention is also contemplated. Generally, but not exclusively, the powder particles of one dose can range in size but are generally 50 microns wide, as compared to a 500 micron wide syringe needle. In other words, powder form vaccines, such as recombinant DNA based vaccines, including Hepatitis B and HIV vaccines; and other medications for treating influenza, tetanus, erectile dysfunction, allergies, pain, cancer, etc., are contemplated. Such powder forms may be admixed with small amounts of sterile water or other physiologically acceptable diluents (e.g., about 1–10%) to form pastes or suspensions. Therefore, adapting the powder injectors to have a means for ejecting a cap and a protective cap and/or film consistent with the present invention is within the ordinary skill in the art.

FIG. 8 is yet another embodiment of the present invention. In this embodiment, the means 20 for removing the cap may comprise an ejection assembly 41, which may comprise a first ejector 43, a second ejector 45, or a hydraulic assembly 66. The first ejector 43 or second ejector 45 may comprise either the nozzle 56 assembly, or the ejector rod 42 assembly. Therefore the means 20 for removing the cap can comprise the following: (a) the nozzle assembly only; (b) the ejector rod 42 assembly only; (c) the hydraulic assembly 66; or (d) or combination thereof.

In this embodiment, the hydraulic assembly 66 is shown comprising a hydraulic piston 82 and a return means 84, such as spring. As the hydraulic fluid is pumped up the hose 68, it travels past the ejector port 88 (with some fluid entering this port) and into the cylinder port 90. As fluid enters the main body 12, it begins to fill up the cylinder chamber 78. As pressure increases in this chamber, the plunger 72 begins to move in the direction of arrow K. In this regard the cylinder piston 76 moves and causes compression of the cylinder spring 80. The piston 76 moves until it reaches a locking position and is locked in place by locking mechanism 86. Since the piston 76 moves in the direction of arrow K, the injector head 70 also moves in that direction. This causes the medication 62 to dispense into the injector chamber 92; ready for injection.

In the meanwhile, as hydraulic fluid flows into the hose 68, some of the fluid will enter the ejector port 88 and cause the ejector piston 48 to move in the direction of arrow L. This causes the ejector rod 42 to contact the nozzle flange 52 on the flange proximal face 33. This will cause movement of the means 46 for biasing the ejector rod, such as spring compression.

As the nozzle flange 52 begins to move in the direction of arrow M, the nozzle sleeve 50 will impact the cap 18. In doing so, the means 54 for biasing the nozzle, such as a spring will move or compress. Thus, as the ejector rod 42 reaches a critical distance, the cap 18 will pop off.

After the cap is popped off and replaced, the medication 62 sits ready for injection into a new cap. The hydraulic fluid pressure is released or reduced. In one embodiment, the as the fluid pressure is reduced, then the means 54 for biasing the nozzle pushes the nozzle back into place; the means 46 for biasing the ejector rod pushes the ejector rod back into place; thereby causing the system to reset. The locking mechanism 86 is then released and the force of the decompressing cylinder spring 80 drives the plunger 72, cylinder piston 76, and the injector head 70 in the direction of arrow N. This pushes the medication 62 into the cap and subsequent patient injection.

While the steps outlined aboveappear to be sequential, they need not be. For example, as the hydraulic fluid pressure is being reduced, the injection may occur when it is made sure that the new cap is sufficiently replaced. The ejector means need not be in a completed reset position before injection can occur.

It should be understood that the foregoing relates only to a limited number of embodiments that have been provided for illustration purposes only. It is intended that the scope of invention is defined by the appended claims and that modifications to the embodiments above may be made that do not depart from the scope of the claims.

We claim:

1. A medical device, comprising:
   (a) a main body comprising proximal and distal ends;
   (b) a protective cap on the main body distal end, and
   (c) an ejection assembly for removing the protective cap from the main body distal end, wherein the ejection assembly comprises an ejection rod and a means for biasing the ejection rod.

2. The medical device of claim 1, wherein the protective cap is adapted to be detachably attached to the main body distal end.

3. The medical device of claim 1, wherein the means for biasing the ejection rod comprises a spring.

4. The medical device of claim 1, wherein the means for biasing the ejection rod comprises a piston.

5. The medical device of claim 4, wherein the means for biasing the ejection further comprises a spring.

6. The medical device of claim 5, wherein the ejection assembly further comprises a proximal port.

7. The medical device of claim 6, wherein the ejection assembly proximal port is in fluid communication with a main body cylinder.

8. A medical device, comprising:
   (a) a main body comprising proximal and distal ends;
   (b) a protective cap on the main body distal end; and
   (c) an ejection assembly for removing the protective cap from the main body distal end, wherein the ejection assembly comprises a nozzle sleeve.

9. The medical device of claim 8, wherein the nozzle sleeve comprises a nozzle flange.

10. The medical device of claim 9, wherein the nozzle sleeve further comprises a means for biasing the nozzle.

11. The medical device of claim 10, wherein the means for biasing the nozzle comprises a nozzle spring.

12. The medical device of claim 11, wherein the ejection assembly further comprises an ejection rod and a means for biasing the ejection rod.

13. The medical device of claim 12, wherein the means for biasing the ejection rod comprises a spring.

14. The medical device of claim 12, wherein the means for biasing the ejection rod comprises a piston.

15. The medical device of claim 11, wherein the means for biasing the ejection rod further comprises a spring.

16. A medical device having a main body, the main body further including a main body proximal end and main body distal end, comprising:
   a) a main body cylinder generally extending from the proximal end to the distal end of the main body;
   b) a hydraulic piston located within the main body cylinder;
   c) a cylinder port fluidly communicating with the main body cylinder;
   d) a nozzle disposed at the distal end of the main body;
   e) a protective cap detachably attached to the nozzle;
   f) an ejection assembly for removing the protective cap from the nozzle; and.
   g) a hydraulic source fluidly connected to the cylinder port and the ejection assembly.

17. The medical device of claim 16, wherein the ejection assembly further comprises an ejection rod, the ejection rod being further adapted to remove the protective cap.

18. The medical device of claim 17, wherein the protective cap comprises a flange, wherein the flange is adapted to communicate with the ejection rod.

19. The medical device of claim 18, wherein the hydraulic source is adapted to permit hydraulic fluid in the hydraulic source to cause the ejector rod to communicate with the protective cap and also, via the cylinder port, to cause movement of the main body hydraulic piston into a cocked position.

20. The medical device of claim 16, wherein the main body is adapted to permit injection of a powder form of a medication.

* * * * *